United States Patent [19]

Richter et al.

[11] 4,388,163

[45] Jun. 14, 1983

[54] METHOD FOR THE INDIRECT OXIDATION OF UREA

[75] Inventors: Gerhard Richter; Erhard Weidlich, both of Erlangen; Konrad Mund, Uttenreuth, all of Fed. Rep. of Germany

[73] Assignee: Siemens Aktiengesellschaft, Munich, Fed. Rep. of Germany

[21] Appl. No.: 310,984

[22] Filed: Oct. 13, 1981

[30] Foreign Application Priority Data

Oct. 27, 1980 [DE] Fed. Rep. of Germany ....... 3040470

[51] Int. Cl.³ .............................................. C25B 1/24
[52] U.S. Cl. .................................. 204/101; 204/128; 204/129; 204/131; 204/252
[58] Field of Search ................. 204/101, 128, 129, 131

[56] References Cited

U.S. PATENT DOCUMENTS

| | | | |
|---|---|---|---|
| 3,692,648 | 9/1972 | Matloff | 204/131 |
| 3,829,370 | 8/1974 | Bonrat | 204/131 |
| 3,909,377 | 9/1975 | Bizot | 204/95 |
| 4,210,501 | 7/1980 | Dempsey | 204/129 |
| 4,214,969 | 7/1980 | Laurance | 204/129 |
| 4,315,805 | 2/1982 | Darlington | 204/129 |

OTHER PUBLICATIONS

Fels, M., "Medical & Biological Engineering and Computing", vol. 16, 1978, pp. 25-30.

Primary Examiner—John F. Niebling
Attorney, Agent, or Firm—Kenyon & Kenyon

[57] ABSTRACT

The invention relates to a method and apparatus for the indirect oxidation of urea by means of an electrochemical cell having two electrodes, to which an aqueous chloride-containing urea solution is supplied, and has as its object the provision of a method such that the urea is removed from the solution as completely as possible, without further changes occurring in the solution. According to the invention, the cell is divided for that purpose by an ion-conducting membrane into two spaces, one of which contains the anode and the other the cathode, and the solution is supplied first to the anode space and then to the cathode space. The method according to the invention serves in particular for extracorporal blood purification.

14 Claims, 3 Drawing Figures

METHOD FOR THE INDIRECT OXIDATION OF UREA

BACKGROUND OF THE INVENTION

The present invention relates to a method for the indirect oxidation of urea by means of an electrochemical cell, having two electrodes, to which an aqueous chloride-containing urea solution is supplied, as well as apparatus for the practice of this method.

Hemodialysis and hemofiltration as well as peritoneal dialysis are methods for the removal of urea from the blood of kidney patients. These treatment methods have become firmly established in the clinical sector and have become routine therapeutic procedures. However, the capacity of the existing dialysis centers is not sufficient for the necessary treatments of the kidney patients. A solution to this situation is home dialysis, which can be carried out by the patient himself. For home dialysis, however it is imperative to reduce the dialysis and substitution solutions required for the patient. Heretofore, in fact, one has discarded the urea-containing electrolyte obtained in extra-corporal plasma regeneration, i.e., in blood purification, the blood filtrate, and a substitution solution had to be available. At present, between 100 and 300 liters of dialysis solution are required per treatment for hemodialysis and about 20 liters of replacement solution for hemofiltration.

Attempts have been undertaken to purify the urea-containing dialysate electrochemically by indirect oxidation of urea. To this end, the dialysate is fed into an electrochemical cell which contains two parallel electrodes in a chamber (cf. "Medical & Biological Engineering and Computing", vol. 16, 1978, pages 25 to 30). An important step here is the formation of hypochlorite, which is formed from the (sodium) chloride present in the dialysate. The following reactions proceed at the electrodes:

Anode: $6Cl^- \rightarrow 3Cl_2 + 6e^-$;
Cathode: $6Na^+ + 6H_2O + 6e^- \rightarrow 6NaOH + 3H_2$.

Provided the anodic and cathodic reaction products, i.e., chlorine and sodium hydroxide, ae thoroughly mixed, hypochlorite then forms:

$$6NaOH + 3Cl_2 \rightarrow 3NaOCl + 3NaCl + 3H_2O.$$

The formed hypochlorite is a strong oxidizing agent, which reacts with the urea in the following manner:
$$(NH_2)_2CO + 3NaOCl \rightarrow N_2 + CO_2 + 2H_2O + 3NaCl.$$

Under favorable conditions, therefore, the urea should be completely transformed into nitrogen, carbon dioxide, and water. In practice, however, it has been found that the conversion is not complete. In addition, a pH shift occurs, and chlorine and hypochlorite remain in the treated liquid, so that a reinfusion with this liquid cannot be performed.

SUMMARY OF THE INVENTION

It is the object of the present invention to process the electrolyte obtained in the plasma regeneration, i.e., the aqueous chloride-containing urea solution, by indirect urea oxidation by means of an electrochemical cell in such a way that the urea is removed as completely as possible, without further changes occurring in the electrolyte. In particular, the processing is to be done in such a way that the purified solution can be re-infused.

According to the present invention this and other objects are achieved by providing that the electrochemical cell is divided by an ion-conducting membrane into two spaces, one of which contains the anode and the other the cathode, and that the solution is supplied first to the anode space and then to the cathode space.

In the method according to the present invention, the aqueous solution to be processed, which, among other things, contains urea and chloride, is conveyed first into the anode space of the electrochemical cell. There, as has been mentioned above, chloride is formed by anodic oxidation of chloride:

$$6Cl^- \rightarrow 3Cl_2 + 6e^-.$$

The chlorine immediately reacts with the urea and converts it oxidatively to nitrogen and carbon dioxide.

$$(NH_2)_2CO + 3Cl_2 + H_2O \rightarrow N_2 + CO_2 + 6H^+ + 6Cl^-.$$

In the anode space, therefore, the pH value of the electrolyte decreases due to the formation of hydrogen ions.

From the anode space the largely urea-free electrolyte passes into the cathode space, where a cathodic evolution of hydrogen takes place:

$$6H^+ + 6e^- \rightarrow 3H_2.$$

Due to the consumption of hydrogen ions and the transport of sodium ions through the membrane from the anode to the cathode space, the pH value rises again and the solution becomes largely neutral. The total reaction of this electrochemical urea oxidation, in which the urea is not removed directly by electrochemical oxidation at the anode, but indirectly by oxidation with anodically developed chlorine, may be written as:

$$(NH_2)_2CO + H_2O \rightarrow N_2 + CO_2 + 3H_2.$$

In the method according to the present invention, the solution to be treated is freed from the urea to a very high degree without harmful by-products being formed. Hence this solution can be re-infused. This results in the advantage that for the (extra-corporal) blood purification no additional liquids, such as dialysis and replacement solutions, are required. Compared with systems for blood purification used until now, there also results a simplification in setup as well as a reduction in size and of cost when using the method of the present invention.

The membrane used in the method according to the present invention is ion-conducting. Moreover, this membrane should be relatively dense in order to prevent diffusion of urea to any large extent. In an especially preferred apparatus for the practice of the method of the present invention, i.e., in an electrochemical cell for indirect urea depletion, the anode space and the cathode space of the electrochemical cell are separated from each other by a cation exchange membrane. This membrane, in fact, should be permeable in particular for sodium ions. In this case it is advantageous also if the flow resistance of the membrane is great against that of the electrolyte spaces, i.e., the anode and cathode spaces. It has been found to be especially advantageous to use for the separation of the electrolyte spaces a membrane of sulfonated polytetrafluoroethylene. Such a membrane, in fact, not only permits the passage of sodium ions, but moreover it is completely inert to chlorine.

In the apparatus according to the present invention, it is further advantageous if the electrodes are porous and fill the electrolyte spaces substantially completely, i.e., if the anode and cathode extend directly up to the membrane separating them. In this manner, substantially no free electrolyte spaces remain; rather, the porous electrode structures essentially take over their function. This results in the advantage that the electrolyte liquid is continuously deviated, so that a mixing favorable to extensive oxidation of the urea occurs. At the same time it is thereby assured that excess chlorine formed in the anode space is completely reduced again in the cathode space.

DETAILED DESCRIPTION OF THE INVENTION

The invention is explained more specifically with reference to the following embodiments and the appended figures.

Figure 1:
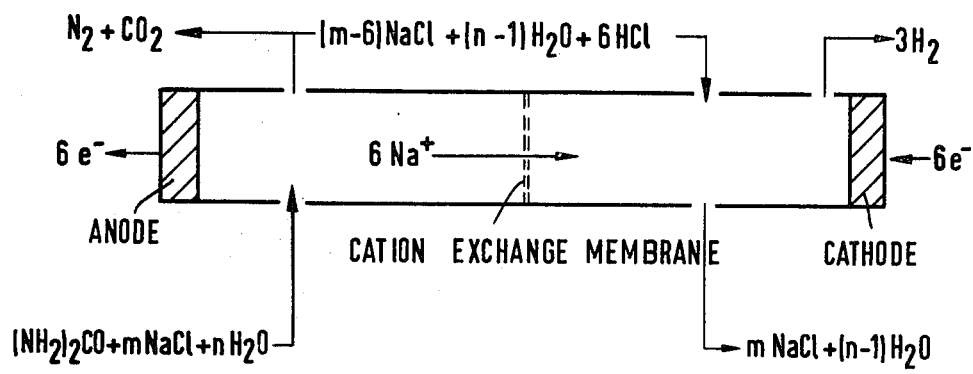

FIG. 1 illustrates—on the basis of a schematically represented electrochemical cell—the principle of the indirect electrochemical urea oxidation taking place in the method of the present invention. As has been set forth above, there occurs at the anode a chlorine evolution (by oxidation of chloride); in the anolyte this chlorine then causes the oxidation of the urea; and, finally, at the cathode the hydrogen ions formed during the urea oxidation are reduced—hydrogen being released.

Figure 2:
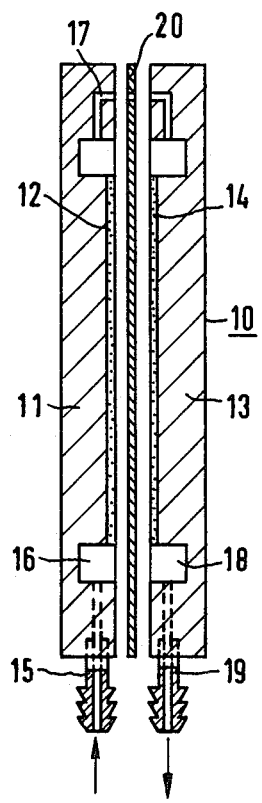

FIG. 2 illustrates—in a kind of "exploded view"—a cross-sectional view of the construction of the electrochemical cell 10 of a preferred embodiment of the apparatus of the present invention. In the recess of a mount 11, for example of polymethacrylate, a porous anode 12 is disposed, and in a mount 13, a porous cathode 14 is disposed. The solution to be treated is supplied via a line 15 to the anode space 16. A line 17 permits the passage of the solution from the anode space 16 into the cathode space 18, from where the solution is removed through a line 19. Between the mounts 11 and 13, an ion-conducting membrane 20 is disposed. In the state ready for operation, the electrodes 12 and 14 apply directly against the membrane 20. The electrical contacts of the two electrodes are not shown in FIG. 2.

In the apparatus of the present invention, the anode consists preferably of activated titanium, in particular in the form of a mesh or expanded metal. Further, the anode may consist of a platinum sheet with one or more meshes of platinum or of platinum and iridium spot-welded thereon. Instead of the meshes, expanded metal of titanium or tantalum may be used which is coated with platinum black or platinum and ruthenium oxide. Another advantageous possibility is to use as the electrode material chlorine-resistant porous metals, such as Raney platinum and porous titanium sponge, or sintered metals, optionally coated with precious noble catalysts.

The cathode consists preferably of an activated carbon fiber mat. The cathode may further consist of a platinum sheet, platinum mesh, vitrious carbon plate, or carbon felt. The carbon felt-as also the carbon fiber mat-may be activated. The activation is effected preferably by heating in air at temperatures between 200° and 700° C., preferably at about 500° C., or in carbon dioxide at temperatures between 500° and 1200° C., preferably at about 1000° C., and/or by coating with platinum or with another noble metal catalyst.

In operation, the blood filtrate flows first through the anode space. There chlorine evolves and the oxidation of the urea takes place. The pH value of the originally, approximately neutral solution then decreases to values between about 1.3 and 1.6, i.e., the solution gives an acid reaction. From the anode space the reaction mixture passes to the cathode space. There the excess chlorine is reduced, and at the same time the pH value of the solution rises again—due to the cathodic reduction of hydrogen ions—to values between about 6.5 and 7.8, i.e., the solution becomes approximately neutral.

By conducting the reaction in the manner stated above, the urea concentration can be reduced, for example, from an initial 2 g/l to approximately 100 mg/l, i.e., the depletion rate is as much as 95%. The degree of urea oxidation depends upon the current density and upon the rate of flow. Thus, the above mentioned values are obtained at a current density of 200 mA/cm$^2$ (electrode size: 60 cm$^2$; temperature: 20° C.). At a current density of 100 mA/cm$^2$ (temperature: 37° C.) the Faraday yield $\gamma$ reaches, at different rates of flow, approximately the following values: 5 cc/min: 0.3; 10 cc/min: 0.45; 20 cc/min. 0.55.

To increase the effectiveness of the apparatus of the present invention, it is advantageous to connect several electrochemical cells in series. In a three-stage arrangement, for example, the urea content can be reduced—at a current of 12 A and a rate of flow of 60 ml/min—from 200 mg/dl to 3 mg/dl, at a Faraday efficiency over 50%. With such an arrangement, 7 grams of urea can be eliminated within one hour and hence one day's urea can be eliminated in about 3 hours.

A thermostat control of the electrochemical cell or cells may be further provided in the apparatus according to the present invention. To this end, the electrolyte spaces are closed off on the sides of the electrodes away from the membrane, for example, by separating sheets of titanium, spaces thereby being formed which can be connected to a thermostat.

In the apparatus according to the present invention, it may be advantageous also to allow the electrochemical cell, or respectively its cathode space, to be followed downstream by one or more reactors for the elimination of traces of hypochlorite. The reactor then preferably is connected electroconductively with the cathode of the electrochemical cell, so that a cathodic reduction of hypochlorite takes place. Preferably, the reactor consists of a tube, in particular of polymethacrylate, which is lined along the wall with a metal mesh and provided with an electric connection; the tube itself is filled with active carbon. The active carbon may be activated and/or coated with platinum or other noble metal catalyst, as can also the carbon fabrics in the cathode of the electrochemical call. In the reactor, platinum-treated carbon advantageously is used. In this case, in fact, the hydrogen potential is adjusted on the platinum-treated carbon, because the electrolyte leaving the cathode space of the electrochemical cell contains hydrogen in dissolved form. In this manner, the residues of hypochlorite—and possibly also of chlorine—can then be removed very easily.

Figure 3:
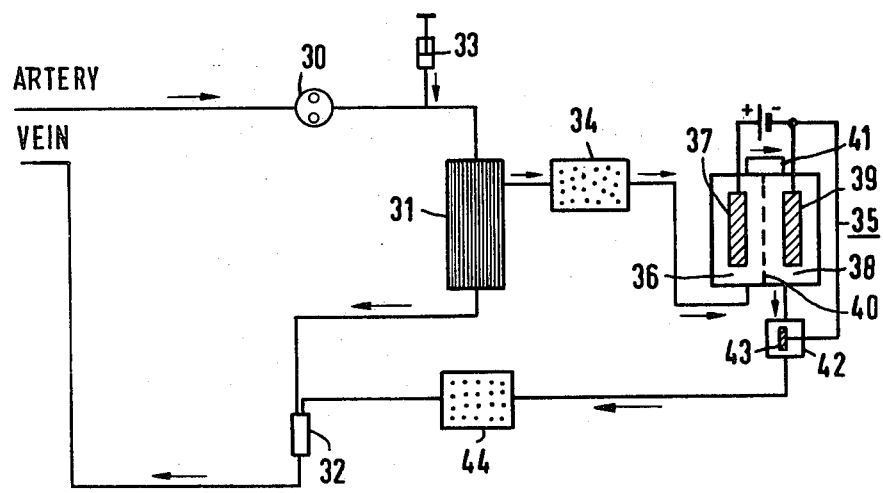

In FIG. 3, there is shown schematically a circuit for the regeneration of blood filtrate, a preferred form of the apparatus according to the present invention being employed. Here blood is taken continuously from a body artery, the blood being supplied by a blood pump 30 to an ultrafilter 31, in which hemofiltration takes place. From the ultrafilter 31 the residual blood returns to the body via a bubble trap 32, being supplied to a vein. Before the hemofiltration, heparin is added to the blood by means of a device 33.

The blood filtrate obtained in the ultrafilter 31 is passed through a carbon filter 34 and is then supplied to the anode space 36 in electrochemical cell 35. The anode space 36, which contains the anode 37, is separated from the cathode space 38 (with the cathode 39) by a membrane 40. The blood filtrate, i.e., the electrolyte, transfers through a line 41 from the anode space 36 to the cathode space 38, and after leaving the cathode space enters a reactor 42. The reactor 42 contains an electrode 43, which is electroconductively connected with the cathode 39 of the electrochemical cell 35. The reactor 42 advantageously is followed downstream by a carbon filter 44, from which the purified blood filtrate is returned—via the bubble trap 32—into the blood circulation. For the conveyance of the blood filtrate, a pump may be provided which is arranged, for example, between the filter 34 and the electrochemical cell 35.

A comparison of the results obtained when carrying out the method according to the present invention with the results of the known method, which operates without separation of the anode and cathode space, shows considerable differences. Thus, in the known process only about 70% of the urea can be converted, while in the method according to the present invention the conversion is almost quantitative. Also, in the known method the pH value of the electrolyte decreases during the urea depletion, i.e., the electrolyte becomes acid, and, moreover, unacceptable residues of chlorine and hypochlorite remain in the electrolyte so that re-infusion is not possible. In the method of the present invention and in the respective apparatus, these disadvantages are avoided by division of the electrolyte space into an anode and a cathode space, where, in the anode space, the urea is first converted and thus removed, and then, in the cathode space, the electrolyte—with the exception of the urea—is brought into equilibrium again, i.e., the original conditions are restored, so that re-infusion can be effected.

What is claimed is:

1. A method for the indirect oxidation of urea in an aqueous chloride-containing urea solution through electrochemical means, comprising:
providing an electrochemical cell containing distinct anode and cathode compartments separated from each other by an ion-conducting membrane, said anode compartment containing the anode of said cell and said cathode compartment containing the cathode of said cell;
supplying said aqueous chloride-containing urea solution to the anode compartment of said electrochemical cell wherein, by means of electrochemical oxidation, chloride is converted to chlorine and urea is then oxidized by said chlorine;
passing said solution to the cathode compartment of said electrochemical cell wherein, by means of electrochemical reaction, hydrogen is formed and evolved; and thereafter removing said solution from the cathode compartment.

2. The method according to claim 1 wherein said membrane is a cation exchange membrane.

3. The method according to claim 2 wherein the resistance of said membrane to flow is high in relation to that of the anode and cathode compartments.

4. The method according to claim 2 wherein said membrane consists of sulfonated polytetrafluoroethylene.

5. The method according to claim 1 wherein said anode and cathode are porous and occupy substantially all of the respective anode and cathode compartments of said electrochemical cell.

6. The method according to claim 1 wherein said anode consists of activated titanium mesh or expanded metal.

7. The method according to claim 1 wherein said cathode consists of an activated carbon fiber mat.

8. The method according to claim 6 wherein said anode is activated with a noble metal.

9. The method according to claim 7 wherein said cathode is activated with a noble metal.

10. The method according to claim 1 wherein said solution removed from the cathode compartment of the cell is thereafter treated to eliminate residues of hypochlorite therefrom.

11. The method according to claim 10 wherein said solution removed from the cathode compartment of the cell is passed through a tubular, active carbon-containing reactor lined along its length with metal mesh, said metal mesh being in electrical connection with the cathode of the electrochemical cell.

12. The method according to claim 11 wherein said active carbon is activated and/or coated with noble metal catalyst.

13. The method according to claim 10 wherein said solution, treated to eliminate residues of hypochlorite therefrom, is thereafter passed through a carbon filter.

14. The method according to claim 1 wherein more than one of said electrochemical cells are arranged in series.

* * * * *